(12) United States Patent
Hungerford et al.

(10) Patent No.: US 8,719,044 B2
(45) Date of Patent: May 6, 2014

(54) COMPUTERIZED METHODS FOR DISPLAYING CLINICALLY-RELATED IN-PATIENT INFORMATION

(75) Inventors: Jill R. Hungerford, Kansas City, MO (US); Charles Cameron Brackett, Overland Park, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 1685 days.

(21) Appl. No.: 11/143,001

(22) Filed: Jun. 2, 2005

(65) Prior Publication Data

US 2006/0277070 A1    Dec. 7, 2006

(51) Int. Cl.
    *G06Q 50/00*    (2012.01)
(52) U.S. Cl.
    USPC ............................................................ 705/2
(58) Field of Classification Search
    USPC .................................................. 705/2–4, 2–3
    See application file for complete search history.

(56) References Cited

U.S. PATENT DOCUMENTS

| | | | |
|---|---|---|---|
| 5,025,374 A * | 6/1991 | Roizen et al. ................. | 600/300 |
| 5,072,383 A * | 12/1991 | Brimm et al. ..................... | 705/2 |
| 5,842,175 A * | 11/1998 | Andros et al. .................... | 705/3 |
| 5,867,821 A | 2/1999 | Ballantyne et al. | |
| 5,946,659 A * | 8/1999 | Lancelot et al. ................. | 705/3 |
| 6,375,077 B1 | 4/2002 | Hankins | |
| 6,789,091 B2 | 9/2004 | Gogolak | |
| 7,076,436 B1 * | 7/2006 | Ross et al. ........................ | 705/3 |
| 2001/0001144 A1 | 5/2001 | Kapp | |
| 2002/0046047 A1 * | 4/2002 | Budd ................................ | 705/1 |
| 2002/0082865 A1 * | 6/2002 | Bianco et al. .................... | 705/2 |
| 2003/0052787 A1 | 3/2003 | Zerhusen et al. | |
| 2003/0069759 A1 * | 4/2003 | Smith ............................... | 705/3 |
| 2003/0163535 A1 * | 8/2003 | Suzuki ......................... | 709/206 |
| 2004/0049407 A1 | 3/2004 | Rosenberg | |
| 2004/0081641 A1 | 4/2004 | Kim et al. | |
| 2005/0080650 A1 | 4/2005 | Noel | |
| 2005/0125255 A1 | 6/2005 | Mockett | |
| 2006/0047538 A1 * | 3/2006 | Condurso et al. ............... | 705/3 |
| 2006/0178913 A1 * | 8/2006 | Lara et al. ........................ | 705/3 |

FOREIGN PATENT DOCUMENTS

GB    2407891 B    6/2008

OTHER PUBLICATIONS

Final Office Action of U.S. Appl. No. 11/303,637, dated Feb. 2, 2010.
Non-Final Office Action mailed Aug. 18, 2009 re U.S. Appl. No. 11/303,637, filed Dec. 16, 2005.
First Action Interview Office Action mailed Jun. 21, 2012 in U.S. Appl. No. 12/981,046.

(Continued)

*Primary Examiner* — Sind Phongsvirajati
(74) *Attorney, Agent, or Firm* — Shook Hardy & Bacon LLP

(57) ABSTRACT

Methods for use in, e.g., in-patient care computing environment, for displaying clinically-related in-patient information on at least one patient-viewable display device are provided. A method in accordance with one embodiment of the present invention may include receiving a clinical order associated with an in-patient, automatically generating one or more tasks based on the clinical order received, and automatically displaying the task(s) on the patient-viewable display device. If desired, the method may additionally include associating the clinical order and the task(s) with an electronic record associated with the in-patient (e.g., an electronic medical record), and accessing the electronic record to obtain the one or more tasks for display on the patient-viewable display device.

9 Claims, 6 Drawing Sheets

(56) References Cited

OTHER PUBLICATIONS

Non-Final Office Action mailed Nov. 9, 2012 in U.S. Appl. No. 12/981,046.

Notice of Allowance and Fees Due in U.S. Appl. No. 11/303,637, mailed Jan. 30, 2012.

* cited by examiner

COMPUTERIZED METHODS FOR DISPLAYING CLINICALLY-RELATED IN-PATIENT INFORMATION

CROSS-REFERENCE TO RELATED APPLICATIONS

Not Applicable.

STATEMENT REGARDING FEDERALLY SPONSORED RESEARCH OR DEVELOPMENT

Not Applicable.

TECHNICAL FIELD

The present invention relates to computing environments. More particularly, embodiments of the present invention relate to methods and systems for use in, e.g., an in-patient care computing environment, the methods and systems for displaying clinically-related in-patient information on at least one patient-viewable display device.

BACKGROUND OF THE INVENTION

In modern clinical settings, there is often an electronic record, e.g., an electronic medical record, associated with each patient presenting at a patient care institution, for example, a hospital or clinic. One example of such an electronic record is an electronic medical record, such as the PowerChart® application available from Cerner Corporation of North Kansas City, Mo. Electronic medical records are designed to offer a single location wherein as much information as possible relevant to the patient with whom the record is associated is readily viewable and actionable, generally by a clinician or other authorized institution personnel.

As information is manually entered into a patient's medical record, or the medical record is automatically populated based on information received from an associated system, events directly affecting the patient's schedule, for instance, tasks, may be generated. "Tasks" are generally used by a clinician or other care giver and serve as reminders that something was, or is, to be done for a particular patient, as well as what was, or is, to be done. That is, "tasks" are typically reminders to the clinician that, for instance, a medication was, or is, to be given, a vital sign was, or is, to be checked, data was, or is, to be collected, a procedure was, or is, to be performed, or the like. Tasks generally have a time associated therewith which may be a particular instance in time or may indicate that the task is continuous, e.g., an IV medication administered over a period of several hours, and specify only an initiation time and/or monitoring time. Alternatively, if desired, a time associated with a task may indicate that a task is to be performed only as needed (i.e., PRN).

Tasks are typically generated from clinical orders and specify, with particularity, what is to be done for a patient. Thus, if an order states that a patient is to receive four 20 mg doses of medication X, one dose every three hours beginning at 12:00 pm, four tasks may be generated for the patient: a first task at 12:00 pm, a second tasks at 3:00 pm, a third task at 6:00 pm, and a fourth task at 9:00 pm, each task indicating that 20 mg of medication X are to be administered.

While this information is generally viewable by the clinician and other authorized institution personnel, the electronic medical record is typically not made available to the patient for viewing. Thus, referring back to the above-described example, although the order setting forth the administration schedule of medication X is known to relevant institution personnel, the patient remains unaware that s/he has particular events scheduled throughout his or her day at 12:00 pm, 3:00 pm, 6:00 pm, and 9:00 pm. In fact, the patient may not be aware that the medication administration has been scheduled for a particular time until the appropriate institution personnel arrives at his or her room to carry out the administration.

This overall unawareness of what is to take place throughout the day can make patients feel out of control and detached from the care they are receiving. In-patient stays in clinical institutions can be nerve-wracking experiences for many individuals and simple knowledge of what's to come in the next few hours can aid dramatically in easing a patient's mind. Further, when unaware of their daily schedules, patients often do not feel at ease to schedule events of their own. For instance, if a particular friend or family member wishes to come to the clinic and visit the patient, the patient is unaware of what might be a good time to instruct the friend or family member to arrive. Still further, if the patient wishes to take a nap or spend some time reading a new book, s/he may get five minutes into it only to find out something else has been scheduled for the same time frame. Events such as this can be extremely frustrating and contribute to overall discontent with a patient's stay at the institution.

Accordingly, a system and method which provides access to information pertaining to an in-patient in a manner which is easily viewable by the in-patient and his or her loved ones would be desirable. Additionally, a system and method for providing a patient access to his or her schedule of events, to the extent such is known to the care-giving personnel, would be advantageous. Further, it would be advantageous if the in-patient could receive this information in real-time so that s/he could feel more in control and at ease with the care being received.

BRIEF SUMMARY OF EMBODIMENTS OF THE INVENTION

Embodiments of the present invention relate to methods for use in, e.g., an in-patient care computing environment, for displaying clinically-related in-patient information on at least one patient-viewable display device. In one embodiment, the method includes receiving a clinical order associated with an in-patient, automatically generating one or more tasks based on the clinical order received, and automatically displaying the task(s) on at least one patient-viewable display device. If desired, the method may further include associating the clinical order and the task(s) with an electronic record associated with the in-patient, and accessing the electronic record to obtain the task(s) for display on the at least one patient-viewable display device. Still further, if desired, the method may additionally include filtering the task(s) based on at least one criterion prior to automatically displaying the task(s) on the at least one patient-viewable display device.

In another embodiment, a method in accordance with the present invention includes receiving at least one of a clinical diagnosis and information pertaining to a clinical issue, the clinical diagnosis and/or clinical issue being associated with an in-patient, automatically generating one or more tasks based on the clinical diagnosis and/or information pertaining to the clinical issue received, and automatically displaying the task(s) on at least one patient-viewable display device.

In yet another embodiment, a method in accordance with the present invention includes receiving at least one of a clinical order, a clinical diagnosis, and information pertaining to a clinical issue, the clinical order, clinical diagnosis, and/or clinical issue being associated with an in-patient, and displaying one or more of advertising content and clinical information pertaining to the clinical order, clinical diagnosis, and/or clinical issue on at least one patient-viewable display device. If desired, the method may further include associating the clinical order, clinical diagnosis, and/or information pertaining to the clinical issue with an electronic record associated with the in-patient, accessing the electronic record to obtain the clinical order, clinical diagnosis, and/or information pertaining to the clinical issue, and utilizing the clinical order, clinical diagnosis, and/or information obtained to select the advertising content and/or clinical information for display on the at least one patient-viewable display device, Still further, if desired, the method may include filtering the advertising content and/or clinical information based on at least one criterion prior to displaying the same on the at least one patient-viewable display device.

The present invention additionally relates to one or more computer-readable media having computer-executable instructions for performing the methods set forth herein, as well as to computers programmed to perform the disclosed methods.

Additional embodiments of the present invention relates to a user interface embodied on at least one computer readable medium, the user interface for displaying an in-patient directed view of clinically-related in-patient information. In one embodiment, the user interface includes a schedule display area configured to display at least one of clinically-related tasks associated with the in-patient and non-clinically-related scheduling information. If desired, a user interface in accordance with embodiments may also include one or more of an advertising content display area configured to display clinically-related advertising content, a clinical information display area configured to display clinically-related education materials, an email display area configured to display one or more of an email inbox associated with the in-patient and at least one email message residing in the in-patient's email inbox, a demographics display area configured to display information associated with the in-patient that has been derived from an electronic record associated with the in-patient, and a live-connect display area configured to display a real-time video image of a remote location with which an audio/video connection has been established.

BRIEF DESCRIPTION OF THE SEVERAL VIEWS OF THE DRAWING

The present invention is described in detail below with reference to the attached drawing figures, wherein:

FIG. 6A is an exemplary screen display illustrating display of clinically-related in-patient information on a patient-viewable display device, in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

The present invention provides a computerized method and system for displaying clinically-related in-patient information on at least one patient-viewable display device. As used herein, the terms "individual", "person", "patient", and "in-patient" are used interchangeably and are not meant to limit the nature of the referenced individual in any way. Rather, the methods and systems described herein are equally applicable in, for instance, a veterinary setting. Further, use herein of the term "patient" and/or "in-patient" is not meant to imply any particular relationship between the individual in question and those accessing, updating, and/or viewing the patient's information.

Additionally, as used herein, the term "patient-viewable display device" refers to a display device viewable by the in-patient, the in-patient's friends, and/or family members of the in-patient, and the like. The term "patient-viewable display device" is thus not intended to imply that the information must be viewable by the individual to whom the information pertains, although such is contemplated by some embodiments of the present invention. The term "patient-viewable display device" is also not intended to imply that the display device must be in proximity to the in-patient. In fact, embodiments of the present invention contemplate that information pertaining to the individual in question may be viewable by individuals outside of the institution, for instance, the information may be viewable by a family member at his or her place of residence. All such variations are contemplated within the term "patient-viewable display device", as that term is utilized herein. In one embodiment, the patient-viewable display device is a flat panel monitor having an interactive touch screen located in proximity to the in-patient and readily available to, e.g., the in-patient and the in-patient's friends and/or family members, at all times.

Having provided a brief overview of embodiments of the present invention, an exemplary operating environment for embodiments of the present invention is described below.

Figure 1:
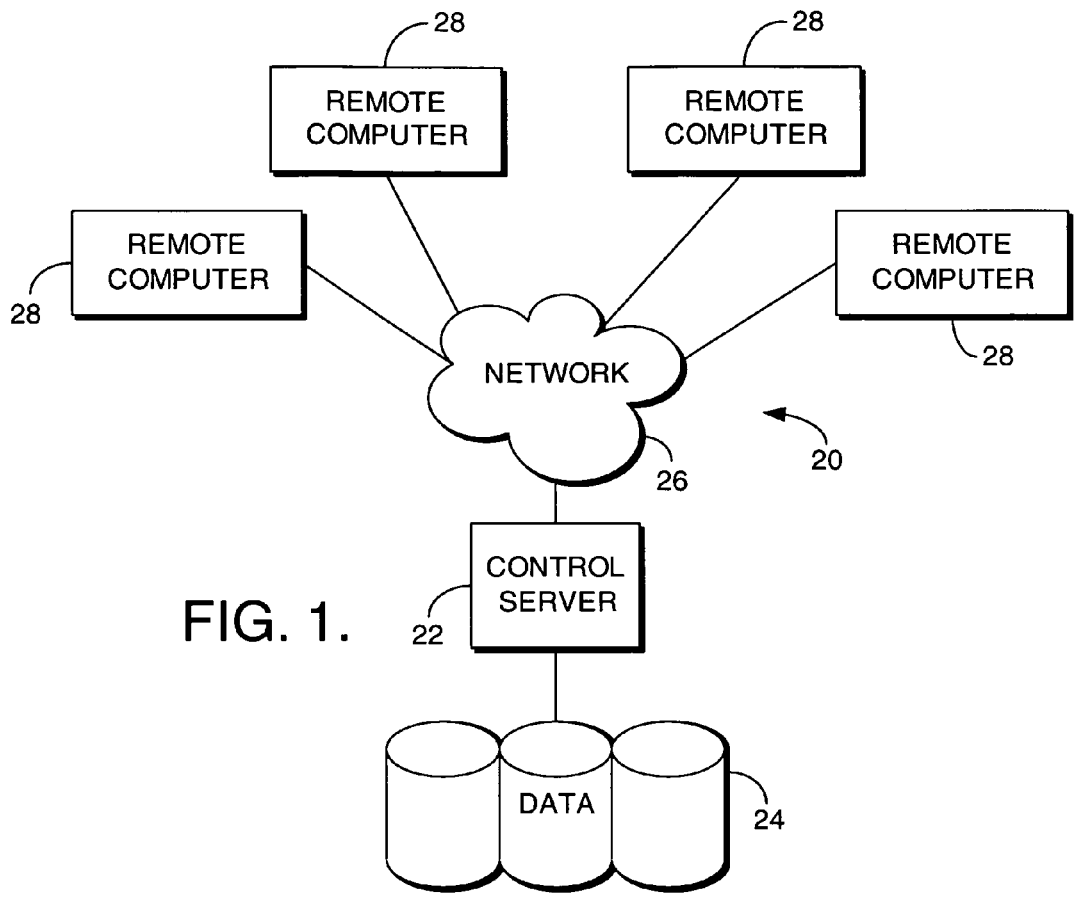
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer readable media, for instance, database cluster 24. Computer readable media can be any available media that may be accessed by control server 22, and includes volatile and nonvolatile media, as well as removable and nonremovable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by control server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for control server 22.

The control server 22 may operate in a computer network 26 using logical connections to one or more remote computers 28. Remote computers 28 may be located at a variety of locations in a medical environment, for example, but not limited to, clinical laboratories, hospitals and other in-patient settings, ambulatory settings, medical billing and financial offices, hospital administration settings, home health care environments, and clinicians' offices. Clinicians may include, but are not limited to, a treating physician or physicians, specialists such as surgeons, radiologists and cardiologists, emergency medical technicians, physicians' assistants, nurse practitioners, nurses, nurses' aides, pharmacists, dieticians, microbiologists, and the like. Remote computers 28 may also be physically located in non-traditional medical care environments so that the entire health care community may be capable of integration on the network. Remote computers 28 may be personal computers, servers, routers, network PCs, peer devices, other common network nodes, or the like, and may include some or all of the elements described above in relation to the control server 22.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in the control server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a user may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. The control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

As previously mentioned, embodiments of the present invention relate to methods for use in, e.g., an in-patient care computing environment, for displaying clinically-related in-patient information on at least one patient-viewable display device. The term "clinically-related in-patient information" as utilized herein, refers to information which is derived from clinical information that has been associated with the in-patient in question. That is, the information to be displayed has particular relevance to the in-patient as it has been selected for display on the basis of clinical information associated with the in-patient. Thus, the information is not randomly selected for display but is information directly affecting, or otherwise of particular interest to, the individual in question.

Figure 2:
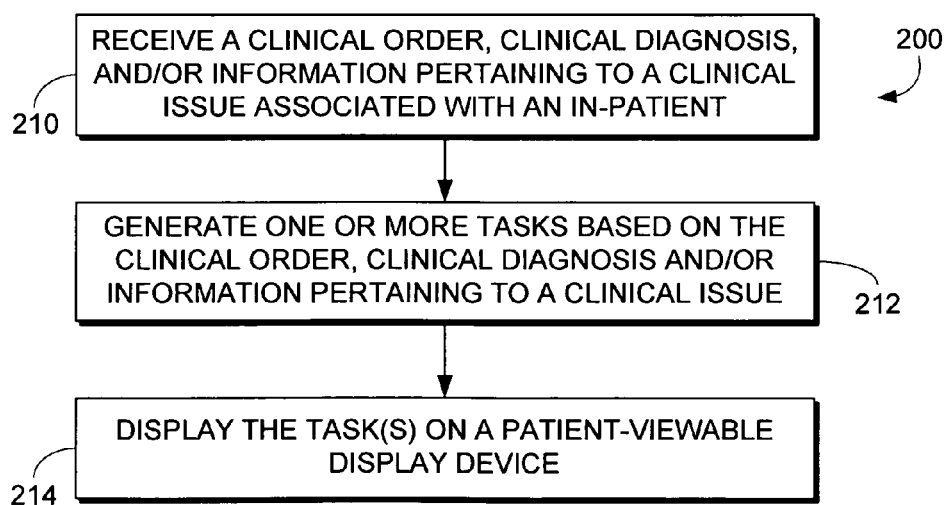
FIG. 2 is a flow diagram showing a method for displaying clinically-related in-patient information in accordance with an embodiment of the present invention.

With reference to FIG. 2, a flow diagram representative of a method for displaying such clinically-related in-patient information in accordance with an embodiment of the present invention is illustrated and depicted generally as reference numeral 200. Method 200 maybe implemented on the above-described exemplary computing system environment (FIG. 1) and, by way of example only, may be utilized by an in-patient in a patient care institution to view his or her daily schedule, Initially, as indicated at block 210, a clinical order, clinical diagnosis, and/or information pertaining to a clinical issue associated with an in-patient is received. Next, as indicated at block 212, one or more tasks are generated based on the clinical order, clinical diagnosis, and/or information pertaining to the clinical issue received. The concept of tasks generated from a clinical order was discussed herein above and may include, by way of example only, a schedule of administration for a particular medication. Typically, clinical orders are thought of as being created by a physician or other appropriate care-giver. However, as the term "clinical order" is utilized herein, an order may also be created by the in-patient. For instance, if an in-patient desires to have the temperature in his or her room decreased at 9:00 pm for more comfortable slumber, s/he may create an order for a room temperature alteration that can cause display of a task to decrease the temperature at 9:00 pm. As all information displayed on the patient-viewable display device, as more fully described below, is also made accessible to the appropriate institution personnel, and as this is likely something the in-patient cannot do him or herself, the appropriate institution personnel can see the task generated from the in-patient-created order and can perform the task at the designated time.

Tasks generated based upon a clinical diagnosis may include, by way of example only, a schedule of tests that are routinely run upon verification of a particular diagnosis, and the like. Tasks generated based upon information pertaining to a clinical issue similarly may include, by way of example only, a schedule of tests that are routinely run upon presentation of a patient with a particular set of symptoms that may be indicative of any number of disparate diagnoses.

Subsequently, as indicated at block 214, the task(s) generated based on the clinical order, clinical diagnosis, and/or information pertaining to a clinical issue associated with an in-patient may be displayed on at least one patient-viewable display device, that is, a computing device monitor, display screen, or the like. The task(s), and any additional information (as more fully described below) may be viewable on multiple display devices, for instance, a display device located in a patient's room, a display device located in an institution waiting area, and/or a display device located at any location remote from the in-patient and/or institution. For instance, in one specific example, the patient-viewable information may be available for viewing on a display device located overseas by military personnel as s/he attempts to monitor the care being received by a loved one.

Additionally, the information displayed may be continuously updated in real-time so that the displayed information changes as care progresses. Accordingly, the in-patient and his or her loved ones may be assured that they are at all times up to speed on the in-patient's care.

Figure 3A:
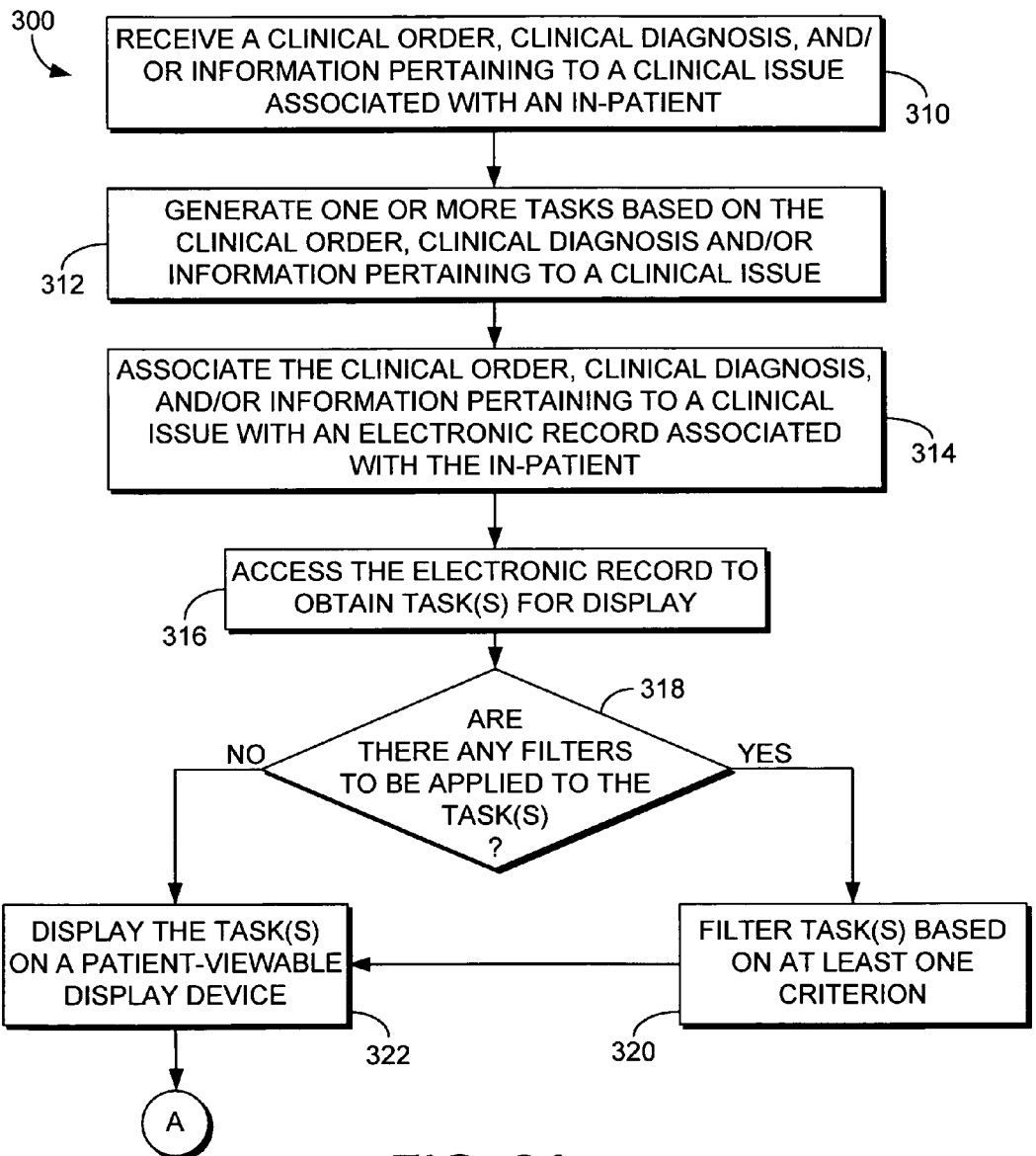
FIGS. 3A and 3B are a flow diagram showing a more detailed method for displaying clinically-related in-patient information than the method of FIG. 2 in accordance with an embodiment of the present invention.
Figure 3B:
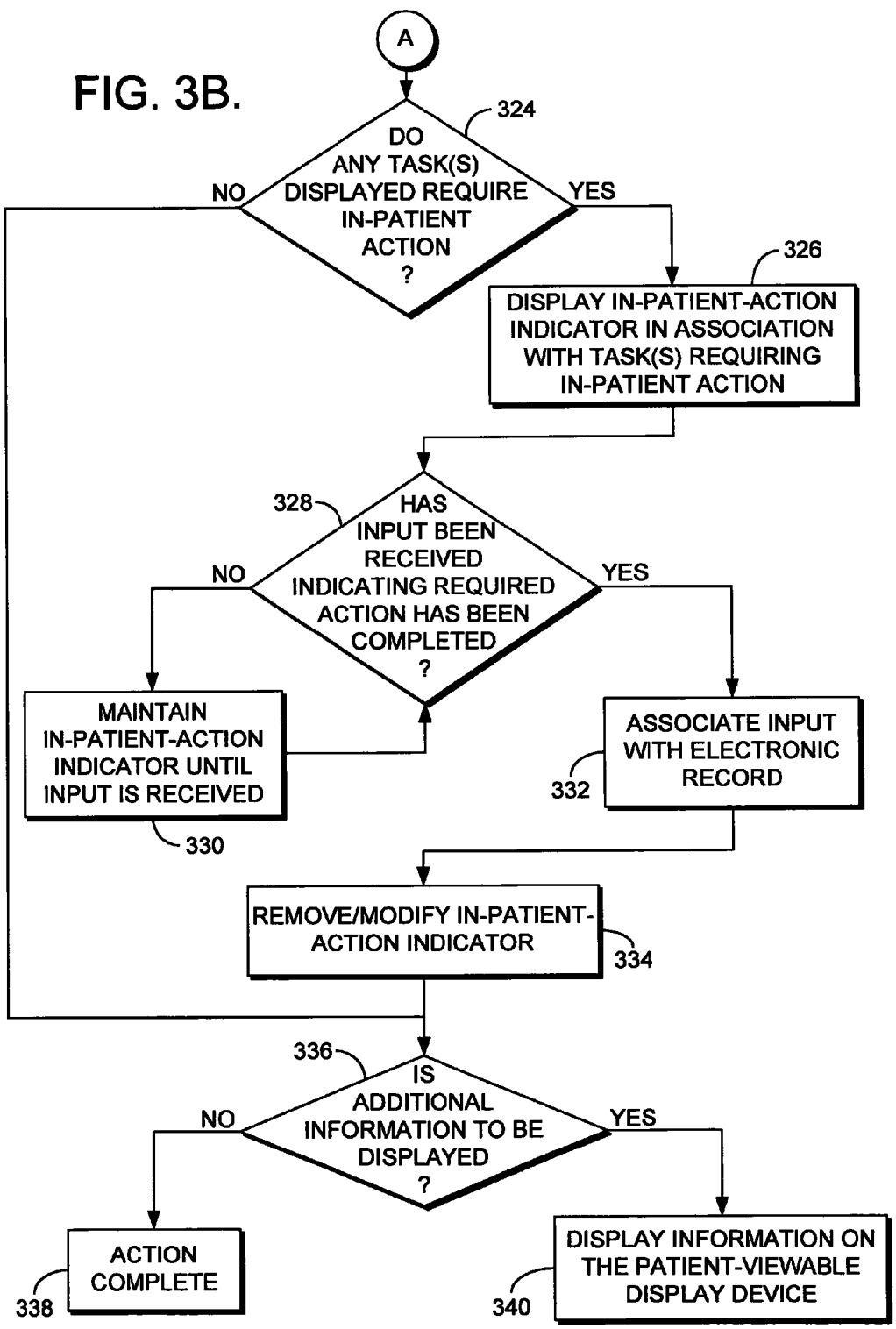

With reference to FIGS. 3A and 3B, a flow diagram is illustrated which shows a more detailedmethod 300 for displaying clinically-related in-patient information on at least one patient-viewable display device than that shown in FIG. 2. Initially, as indicated at block 310, a clinical order, clinical diagnosis, and/or information pertaining to a clinical issue associated with an in-patient is received. Next, as indicated at block 312, one or more tasks are generated based on the clinical order, clinical diagnosis, and/or information pertaining to the clinical issue received. Each of steps 310 and 312 was discussed more fully herein above with reference to steps 210 and 212, respectively, of FIG. 2.

Subsequently, as indicated at block 314, the clinical order, clinical diagnosis, and/or information pertaining to a clinical issue associated with the in-patient is associated with an electronic record associated with the in-patient, e.g., an electronic medical record, such as the PowerChart® application available from Cerner Corporation of North Kansas City, Miss. By providing association with an electronic record, all information displayed (as more fully described below) may be automatically updated in real-time, providing up-to-the-minute relevant information to in-patients and their loved ones.

Next, as indicated at block 316, the electronic medical record is accessed to obtain tasks for display. In one embodiment, all tasks generated at the step indicated at block 312 initially may be accessed.

It is next determined whether or not there are any filters to be applied to the task(s) obtained. This is indicated at block 318. Filters may include, by way of example only, filtering criteria specified by a care-giver, filtering criteria specified by the in-patient, and/or filtering criteria specified by the institution. A care-giver-specified filtering criterion may be, by way of example only, an instruction that procedures automatically scheduled on the basis of a particular lab test result not be made available for display until specifically directed by the care-giver, such instruction being provided only subsequent to the lab test result being explained to the patient. An in-patient-specified criterion may be, by way of example only, an instruction that the patient wishes only to be informed of those tasks which cause interruption to the patient and not of those tasks which may be performed by institution personnel without the patient being disturbed. An institution-specified criterion may be, by way of example only, an instruction that all patients scheduled to undergo surgical procedures be informed of the risks associated with such procedures prior to the procedure being displayed on the patient's schedule.

If it is determined at the step indicated at block 318 that one or more filters are to be applied to the task(s) obtained, the filters are subsequently applied and the task(s) are filtered based upon at least one criterion. This is indicated at block 320. Subsequently, or if it is determined that no filters are to be applied to the task(s) obtained, the task(s) are displayed on at least one patient-viewable display device, as indicated at block 322.

Turning now to FIG. 3B, it is next determined whether any of the task(s) displayed require in-patient action. This is indicated at block 324. By way of example only, in order for an institution to perform certain surgical procedures, the in-patient must be made aware of the risks associated with the procedure and execute a consent therefore. In this instance, a task stating, e.g., "Read and Sign Consent" may be generated and completion of such task may be required prior to the surgical procedure taking place. If it is determined that a particular task requires in-patient action, an in-patient-action indicator may be displayed in association with the task, as indicated at block 326. An exemplary in-patient-action indicator is shown and described more fully below with reference to FIG. 6A.

If an in-patient-action indicator has been displayed in association with a particular task, it is next determined whether input has been received indicating that the in-patient-required action has been completed. This is indicated at block 328. That is, referring to the above-described "Read and Sign Consent" task, it may be determined whether input has been received which indicates that such consent has been executed. If such input has not been received, the in-patient-action indicator is maintained in association with the task which requires action until such input is received, as indicated at block 330. However, if input is received which indicates that the required action has been completed, such input is subsequently associated with the electronic record associated with the in-patient, e.g., the electronic medical record. This is indicated at block 332. In this way, the care giving institution may track compliance with certain regulatory requirements with increased ease.

Additionally, in one embodiment, input may be received which indicates that a particular patient or his/her representative has refused to execute a requested consent or that a previously executed consent has been modified or canceled. As the input is integrated with an electronic record associated with the in-patient, if such modification, cancellation, or refusal input is received, the relevant clinician and/or other institution personnel may be automatically notified and/or the consent may be automatically identified as no longer effective as originally executed. Further, any procedures which have already been scheduled may be canceled pending receipt of the appropriate consent with or without accompanying notice to the relevant clinician and/or other institution personnel.

The in-patient-action indicator may subsequently be removed from association with the task which required in-patient action or may be modified to indicate that the required action has been completed, as indicated at block 334.

If it is determined that no displayed tasks require in-patient action, or upon removal or modification of the in-patient-action indicator for any tasks for which in-patient action was required, it is subsequently determined whether any additional information is to be displayed. This is indicated at block 336. Additional information may include additional clinically-related information, such as, by way of example only, educational materials explaining procedures scheduled to be performed for the in-patient or setting forth the potential side effects of medications the in-patient is scheduled to receive, educational materials mandated by Joint Commission on Accreditation of Healthcare Organizations (JCAHO) requirements, support group information, patient surveys, and/or selectable links thereto.

In one embodiment, the electronic record associated with the in-patient may also be integrated with the institution's billing system, e.g., the ProFit® system available from Cerner Corporation of North Kansas City, Miss. If such integration exists, additional information may further include a summary or itemized listing of charges the in-patient has incurred during their stay, such charge-related information being displayed, e.g., a pre-determined number of hours prior to the in-patient's discharge from the institution. Alternatively, charge-related information may be displayed as a task which may or may not require in-patient action, e.g., review and/or acceptance or modification prior to discharge.

Additional information may also include information which the in-patient may be interested in but which is not clinically-related, for instance, institution visiting hours or chapel service schedules, email communications, electronic messages, meal menu choices, and selectable links thereto.

If it is determined that no additional information is to be displayed, action is complete, as indicated at block 338. If it is determined that additional information is to be displayed, such additional information is subsequently displayed on the patient-viewable display device, as indicated at block 340.

It will be understood and appreciated by those of ordinary skill in the art that the steps indicated at block 336, 338 and 340 may be performed at any time during the method set forth in FIGS. 3A and 3B and that waiting, for instance, until decisions on in-patient-action items have been resolved is optional and not intended to limit the present invention in any way. For instance, additional information may be displayed contemporaneously with display of tasks on the patient-viewable display device or may be displayed prior to or independently of any tasks being received, if desired. Additionally, determinations regarding display of additional information may be performed multiple times as additional inputs and/or changes in displayed information become available. All such variations are contemplated to be within the scope hereof.

Figure 4:
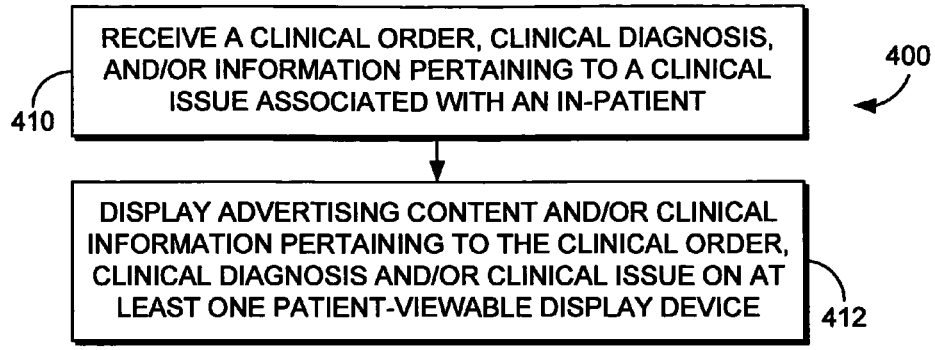
FIG. 4 is a flow diagram showing a method for displaying clinically-related advertising content and/or clinical information in accordance with an embodiment of the present invention.

Turning now to FIG. 4, a flow diagram is illustrated which shows a method 400 for displaying clinically-related advertising content and/or clinical information on at least one patient-viewable display device in accordance with an embodiment of the present invention. Such advertising content may include, by way of example only, advertising for a particular medication a patient has been scheduled to receive, which advertising may encourage the patient to select the name brand instead of the generic formulation of the medication. Clinical information may include, by way of example only, educational materials explaining procedures scheduled to be performed for the patient or setting forth the potential side effects of medications the patient is scheduled to receive, educational materials mandated by JCAHO requirements, support group information, and/or selectable links thereto.

Initially, as indicated at block 410, a clinical order, clinical diagnosis, and/or information pertaining to a clinical issue associated with a patient is received. Examples of each of these was discussed herein above with reference to FIGS. 2, 3A, and 3B. Subsequently, as indicated at block 412, advertising content (that is, clinically-related advertising content) and/or clinical information pertaining to the clinical order, clinical diagnosis, and/or clinical issue is displayed on at least one patient-viewable display device, for instance, a computing device monitor or the like.

Figure 5:
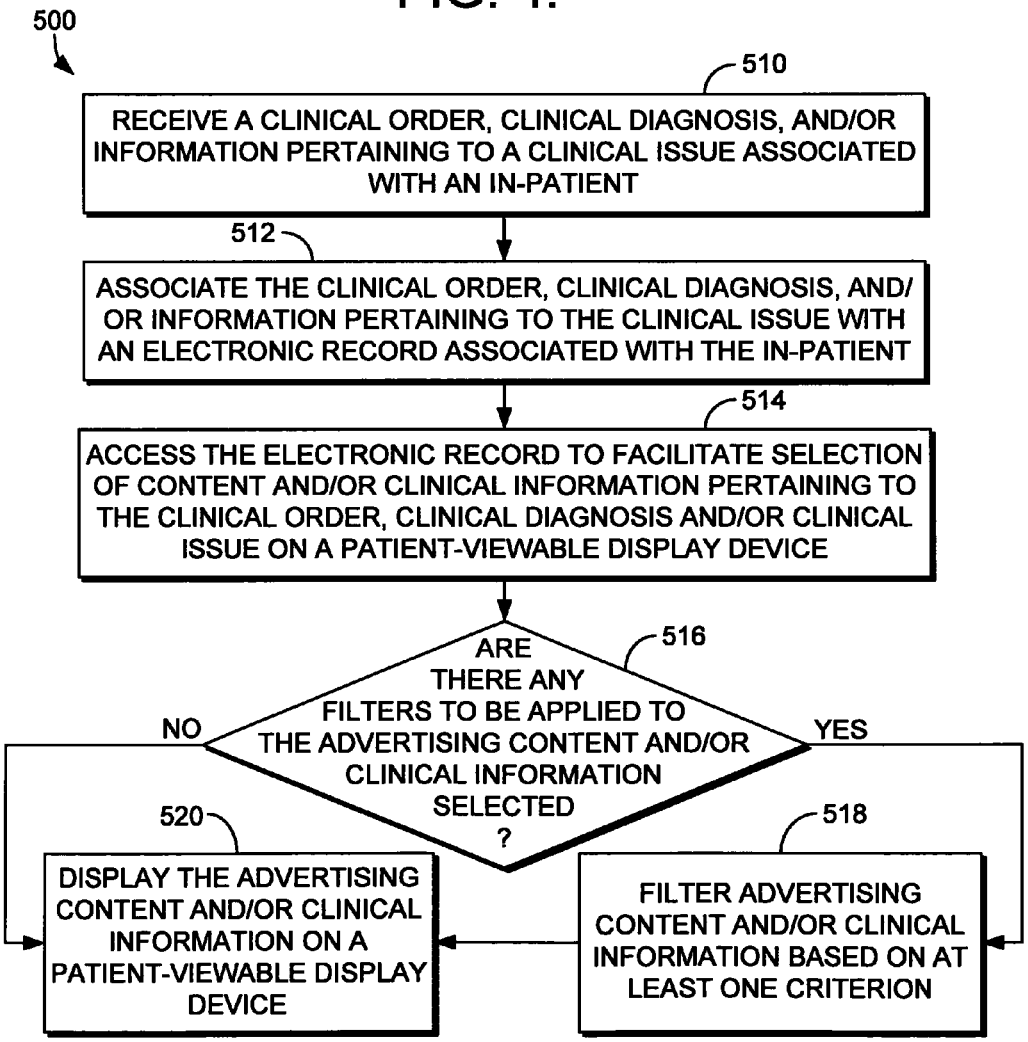
FIG. 5 is a flow diagram showing a more detailed method for displaying clinically-related advertising content and/or clinical information than the method of FIG. 4 in accordance with an embodiment of the present invention.

With reference to FIG. 5, a flow diagram is illustrated showing a more detailed method 500 for displaying clinically-related advertising content and/or clinical information than the method of FIG. 4 in accordance with an embodiment of the present invention. Initially, as indicated at block 510, a clinical order, clinical diagnosis, and/or information pertaining to a clinical issue associated with an in-patient is received. Subsequently, the clinical order, clinical diagnosis, and/or information pertaining to the clinical issue is associated with an electronic record associated with the in-patient, e.g., an electronic medical record, such as the PowerChart® application available from Cerner Corporation of North Kansas City, Miss. This is indicated at block 512. Subsequently, as indicated at block 514, the electronic record is accessed to obtain the clinical order, clinical diagnosis, and/or information pertaining to the clinical issue, the clinical order, clinical diagnosis, and/or information pertaining to the clinical issue is utilized to select clinically-related advertising content and/or clinical information for display, and the clinically-related advertising content and/or clinical information is displayed on at least one patient-viewable display device.

Next, it is determined whether there are any filters to be applied to the clinically-related advertising content and/or clinical information selected, as indicated at block 516. As previously described with respect to step 320 of FIG. 3A, such filters may set forth at least one care giver-specified criterion, in-patient-specified criterion, or institution-specified criterion. If any filters are to be applied, the advertising content and/or clinical information is subsequently filtered based on at least one criterion, as indicated at block 518. Subsequently, or if no filters are to be applied, the clinically-related advertising content and/or clinical information is displayed on at least one patient-viewable display device. This is indicated at block 520.

Figure 6A:
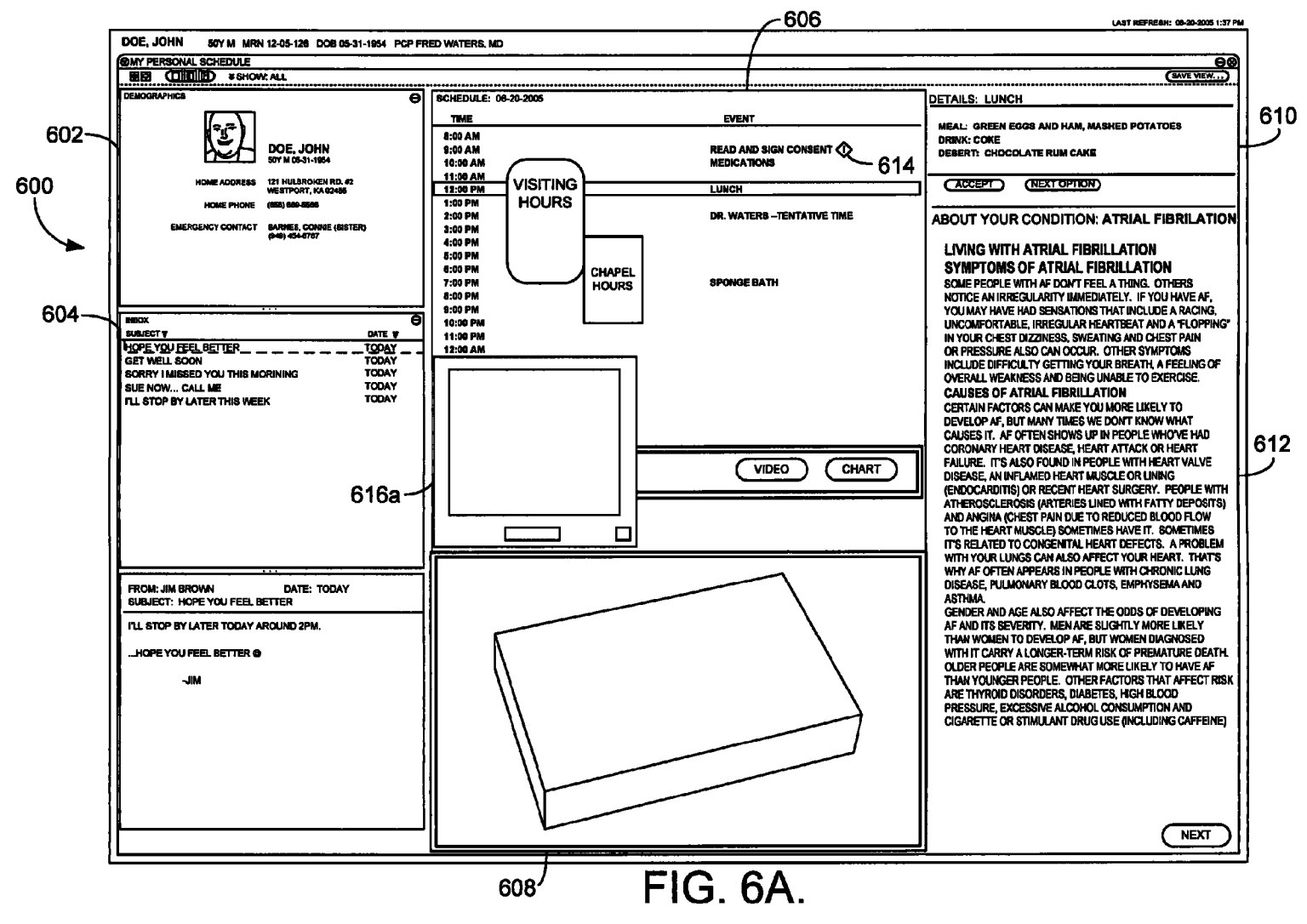

Turning now to FIG. 6A, an exemplary screen display illustrating display of clinically-related in-patient information on a patient-viewable display device, in accordance with an embodiment of the present invention, is illustrated and designated generally as reference numeral 600. It will be understood and appreciated by those of ordinary skill in the art that the screen display of FIG. 6A is provided by way of example only and it is not intended to limit the scope of the present invention in any way. Further, it will be understood and appreciated that the screen display 600 of FIG. 6A may be customized by the in-patient (or other authorized person) such that only those items which he or she wishes to view are displayed. All such variations are contemplated to be within the scope hereof.

Screen display 600 includes a demographics display area 602, an email display area 604, a schedule display area 606, an advertising content display area 608, a menu display area 610, and an additional information display area 612. The demographics display area 602 includes basic information about the in-patient to whom the displayed information pertains, such information being derived from an electronic record associated with the in-patient. For example, the demographics display area 602 includes the patient's name, age, date of birth, home address, home telephone number, and emergency contact information, in addition to a picture of the patient. The email display area 604 includes an inbox and a viewing area so that the patient can check his or her email, if desired. The schedule display area 606 includes clinically-related tasks that have been scheduled for the in-patient's day (in accordance with the above-described methods), as well as additional non-clinically-related scheduling information such as institution visiting hours and a chapel service schedule.

Note that one of the tasks on the patient's schedule includes an in-patient-action indicator 614 in the form of a diamond with an exclamation point inside. This indicator indicates that in-patient action is required on this particular task before, for instance, a particular procedure may be performed. It will be understood and appreciated by those of ordinary skill in the art that the particular form of the in-patient-action indicator is shown by way of example only and that any indicator serving to inform the in-patient and/or his or her loved ones that action is required is contemplated to be within the scope of the present invention.

The advertising content display area 608 includes any clinically-related advertising content that has been selected for the in-patient based upon the above-described methods. The menu display area 610 includes meal menu information and permits the in-patient to browse through options, if available, and select the meal of his or her choice, if appropriate. The additional information display area 612 includes information, in this case clinically-related information, for the patient to review, if desired. As previously discussed, such clinically-related information may include, by way of example only, educational materials explaining procedures scheduled to be performed for the in-patient or setting forth the potential side effects of medications the in-patient is scheduled to receive, educational materials mandated by JCAHO requirements, support group information, and/or selectable links thereto.

Figure 6B:
FIG. 6B is an exemplary screen display similar to that shown in FIG. 6A and additionally illustrating live-connect functionality through an audio/video connection, in accordance with an embodiment of the present invention.

The screen display 600 of FIG. 6A additionally includes a live-connect display area 616a wherein the in-patient may view a connection established via an audio/video connection with another person in a remote location if appropriate capability is available. Such other person may be a family member or the like located at his or her residence, or may be another institution in-patient, e.g., the baby of an in-patient woman who has recently given birth. The live-connect display area 616a of FIG. 6A is not active. However, in the similar view of FIG. 6B, the live-connect display area 616b is illustrated showing a live connection.

In operation, by way of example only, suppose a diabetic patient presented to the emergency department of a particular institution complaining of chest pain and, after being examined, was admitted to the institution with an admitting diagnosis of Acute Myocardial Infarction (AMI). During the patient's stay, s/he underwent a Diagnostic Cardiac Catheterization yielding a diagnosis of 75% stenosis of the Mid-LAD, 85% stenosis of the proximal RCA, and 90% stenosis of the distal LAD. The patient, however, did not undergo an intervention due to the specific circumstances at the time. The intervention is accordingly scheduled for the following day. The patient is wheeled back to his or her room to recover from the Catheterization procedure. After recovering, the patient is interested in viewing information related to his/her stay to see what the next steps are along with what the available options are for dinner.

Upon accessing his/her information, an initial screen display appears, e.g., the screen display illustrated in FIG. 6A. The patient's calendar shows a range of two days displaying today's and tomorrow's schedule. The patient when s/he arrived back in the room and when the doctor is schedule to visit to review the procedure results. Further, the patient sees that s/he is scheduled for an intervention the following day at 9:00 am. On the right-hand side of the screen, is education information about coronary artery blockage (the patient's diagnosis). Further, they see educational information about interventional cardiac catheterization (the procedure s/he will be having the next day). A check box appears for the educational material providing the capability of capturing the fact that the patient acknowledged reading the material.

Also on the screen is the patient's dinner plan. The schedule shows it arriving at 7:00 pm. To the right, it shows a scheduled meal tailored for his/her diabetic needs. The electronic record associated with the patient had diabetes listed so the meal planning system was automatically trigger to provide only diabetic meals. The patient sees that asparagus is listed for their meal. The patient, however, doesn't care for asparagus, so he selects the "Next Option" indicator which causes display of another diabetic-formulated meal. As soon as the patient sees an offering that s/he likes, s/he selects the "Accept" indicator which causes notification to be forwarded to the kitchen that the patient in Room 121 has requested a particular meal.

On the medications front, the patient has been prescribed Plavix to thin their blood. In addition to the Plavix blood thinning educational material being displayed, advertising content related to alternatives for blood thinners are also displayed on the screen.

The patient schedule indicates that the cardiologist will arrive in the room at 3:30 pm to review the results with the patient and family. When the cardiologist arrives, he is able to select the Diagnostic Cardiac Catheterization procedure shown on the schedule that had taken place at 10:00 am that morning. Upon selecting this item, the system asks the user to sign in with a logon and password. Once the cardiologist has input the appropriate information, the images of the procedure are available for display so that the cardiologist may discuss the findings and explain the interventional procedure that will be done the following day.

As can be understood, the present invention provides methods and systems for use in, e.g., an in-patient care computing environment, the methods and systems for displaying clinically-related in-patient information on at least one patient-viewable display device. Utilizing the methods and systems described herein, in-patients and their loved ones are able to more actively participate in the care of themselves and/or their friends and family in a way that permits them to have an increased feeling of control over the care being received. This, in turn, not only provides for increased safety but leads to a more contented in-patient stay.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and is within the scope of the claims.

What is claimed is:

1. A computer-implemented method for displaying clinically-related in-patient information, the method comprising:
receiving at a first computing device an indication of a lab result of an inpatient;
automatically generating a task that is based on the lab result and that indicates a surgical procedure;
storing the task in a database as part of an electronic medical record of the inpatient;
retrieving the task from the electronic medical record to enable the task to be displayed on in a patient-specific graphical user interface;
determining that the task indicating the surgical procedure is proscribed from being displayed in the patient-specific graphical user interface until a caregiver has logged in by way of the patient-specific graphical user interface; and
upon receiving login credentials of the caregiver by way of the patient-specific graphical interface, displaying the task indicating the surgical procedure in the patient-specific graphical user interface.

2. The computer-implemented method of claim 1, wherein the task includes a charge-related task.

3. The computer-implemented method of claim 1, further comprising displaying an in-patient-action indicator in association with the task, wherein the in-patient-action indicator includes a graphical user interface icon that is displayed adjacent to the task and that indicates to the in-patient that a consent form must be executed for the patient.

4. The computer-implemented method of claim 3 further comprising,
determining that the consent form has not been executed,
automatically notifying institution personnel that are relevant to the in-patient that the task has not been completed, and
canceling a procedure that has already been scheduled and that requires completion of the task before the procedure is allowed to be started.

5. The computer-implemented method of claim 1, further comprising displaying additional information on the patient-viewable display device.

6. The computer-implemented method of claim 5, wherein the additional information comprises one or more of educational materials, support group information, patient surveys, charge-related information, service schedules, institution visiting hours, email communications, electronic messages, available menus, and selectable links thereto.

7. The computer-implemented method of claim 1 further comprising, displaying the task on an additional patient-viewable display device.

8. A computer-implemented method for displaying clinically-related inpatient information, the method comprising:
receiving at least one of a clinical diagnosis and information pertaining to an indication of a lab result, the at least one of the clinical diagnosis and information pertaining to the indication of the lab result, being associated with an inpatient;
automatically generating a task based on the at least one of the clinical diagnosis and the information pertaining to the indication of the lab result, that was received;
storing the task in a database as part of an electronic medical record of the inpatient;
accessing the database to retrieve the task to be displayed on a patient-specific graphical user display device;
determining that the task is proscribed from displayed on the patient-specific graphical user display device until a caregiver has logged in by way of the patient-specific display device indicating that the care-giver has explained to the inpatient the at least one of the clinical diagnosis and the information pertaining to the indication of the lab result; and
upon receiving the caregiver's credentials, displaying the task on a patient-specific graphical user display device.

9. One or more computer memory devices storing computer-executable instructions that, when executed by a computing device, perform operations for
displaying clinically-related in-patient information, the operations comprising: receiving an indication of a lab result of an inpatient;
leveraging a processor to automatically generate a task that is based on the lab result and that includes a scheduled procedure,
storing the task in a database as part of an electronic medical record of the inpatient;
retrieving the task from the electronic medical record to enable the task to be displayed on a patient-specific display device;
determining that the task is proscribed from displayed on the patient-specific display device until a caregiver has logged in by way of the patient-specific display device indicating that the care-giver has explained the lab result to the inpatient; and upon receiving the caregiver's credentials, displaying the task indicating the scheduled procedure on a patient-specific display device.

\* \* \* \* \*